United States Patent
Alshemari

(10) Patent No.: US 8,529,580 B1
(45) Date of Patent: Sep. 10, 2013

(54) SURGICAL GRASPING INSTRUMENT WITH U-SHAPED JAWS IN COMBINATION WITH A TYMPANOSTOMY TUBE

(71) Applicant: Hasan M. Sh. Sh. Alshemari, Saad Al-Abdulla (KW)

(72) Inventor: Hasan M. Sh. Sh. Alshemari, Saad Al-Abdulla (KW)

( * ) Notice: Subject to any disclaimer, the term of this patent is extended or adjusted under 35 U.S.C. 154(b) by 0 days.

(21) Appl. No.: 13/666,653

(22) Filed: Nov. 1, 2012

(51) Int. Cl.
*A61F 11/00* (2006.01)

(52) U.S. Cl.
USPC ........................................ 606/109; 606/207

(58) Field of Classification Search
USPC ............... 606/1, 205–210, 139, 144, 148, 57, 606/167, 170, 174, 109; 81/346, 381, 420, 81/426; 604/8–10
See application file for complete search history.

(56) References Cited

U.S. PATENT DOCUMENTS

| | | | |
|---|---|---|---|
| 984,756 A * | 2/1911 | Frisch | 606/174 |
| 3,814,102 A | 6/1974 | Thal | |
| 4,043,343 A * | 8/1977 | Williams | 606/207 |
| 4,205,681 A | 6/1980 | Nestor et al. | |
| 4,243,047 A | 1/1981 | Olsen | |
| 4,369,788 A | 1/1983 | Goald | |
| 4,522,206 A | 6/1985 | Whipple et al. | |
| 4,803,983 A * | 2/1989 | Siegel | 606/151 |
| 4,950,275 A | 8/1990 | Donini | |
| 5,383,877 A * | 1/1995 | Clarke | 606/148 |
| 5,489,286 A * | 2/1996 | Cinberg et al. | 606/109 |
| 5,851,214 A * | 12/1998 | Larsen et al. | 606/170 |
| 6,063,103 A | 5/2000 | Hashiguchi | |
| 6,245,077 B1 * | 6/2001 | East et al. | 606/109 |
| 6,752,823 B2 | 6/2004 | Prestel | |
| 6,889,694 B2 * | 5/2005 | Hooven | 128/898 |
| 7,097,661 B2 * | 8/2006 | Perry | 623/10 |
| 2005/0085850 A1 * | 4/2005 | Harris et al. | 606/205 |
| 2006/0184197 A1 | 8/2006 | Shifrin et al. | |
| 2009/0259248 A1 | 10/2009 | Ganter et al. | |
| 2010/0023050 A1 * | 1/2010 | Reinauer et al. | 606/207 |
| 2011/0046661 A1 * | 2/2011 | Kuehn | 606/206 |

FOREIGN PATENT DOCUMENTS

FR  2 694 179j  2/1994

OTHER PUBLICATIONS http://www.thefreedictionary.com/Ball, note entry #4, definition of Ball retrived Feb. 26, 2013.*

* cited by examiner

*Primary Examiner* — Ryan Severson
*Assistant Examiner* — David Eastwood
(74) *Attorney, Agent, or Firm* — Richard C. Litman

(57) ABSTRACT

The surgical grasping instrument having U-shaped jaws has a pair of handles connected to a pair of U-shaped jaws by a pair of elongated arms. The lower jaw is rigidly connected to the anterior end of the lower elongated arm. The upper jaw is pivotally connected to the anterior ends of the upper and lower elongated arms. The upper and lower arms are held together in sliding contact so that sliding the upper arm pivots the upper jaw. Both handles have finger loops. The rearward handle is rigidly attached to the lower arm, and is pivotally attached to the forward handle. The forward handle is attached to the upper arm by a ball and socket joint so that pivoting the handles pivots the upper jaw. The U-shaped jaws are designed to grasp round or semi round objects, such as a tympanostomy tube.

12 Claims, 5 Drawing Sheets

SURGICAL GRASPING INSTRUMENT WITH U-SHAPED JAWS IN COMBINATION WITH A TYMPANOSTOMY TUBE

BACKGROUND OF THE INVENTION

1. Field of the Invention

The present invention relates to surgical instruments, and particularly to a surgical grasping instrument having U-shaped jaws.

2. Description of the Related Art

Myringotomy is a surgical procedure in which a tiny incision is made in the tympanic membrane (the eardrum) in order to relieve pressure caused by the excessive build-up of fluid, or to drain pus. Typically, a myringotomy procedure is accompanied by the insertion of a tympanostomy tube or ventilation ear tube in the tympanic membrane. This tube has a round or oval shape and flanged ends, and is inserted into the external auditory canal and seated in the tympanic membrane with the flanged ends on opposite sides of the membrane to keep the tube in place. During the procedure, the ventilation ear tube is held by a forceps. Due to the extremely small size of the ventilation tube, as well as the sensitivity of the eardrum and the middle ear, precautionary steps are taken to prevent permanent damage to the patient during tube placement. Thus, this sensitive operation gives rise to considerable challenges to a surgeon's dexterity and patience.

Conventional forceps have a pair of straight, opposing jaws that only permit grasping a round or semi round surface of an object or body tissue during the surgery. The jaw part does it only from on one side, on a specific area on which the holding stability is reduced. As shown in FIG. 6, grasping the round surface of the interior or exterior flange of the tympanostomy tube on a single flange position renders the tube hard to manipulate into the desired position(s). Thus, a surgical grasping instrument having U-shaped jaws solving the aforementioned problems is desired.

SUMMARY OF THE INVENTION

The surgical grasping instrument having U-shaped jaws has a pair of handles connected to a pair of U-shaped jaws by a pair of elongated arms. The lower jaw is rigidly connected to the anterior end of the lower elongated arm. The upper jaw is pivotally connected to the anterior ends of both the upper and lower elongated arms. The upper and lower arms are held together in sliding contact so that sliding the upper arm pivots the upper jaw. Both handles have finger loops. The rearward handle is rigidly attached to the lower arm. The forward handle is pivotally attached to the rearward handle, and is also attached to the upper arm by a ball and socket joint so that pivoting the handles pivots the upper jaw. The U-shaped jaws are dimensioned and configured to grasp round or semi-round objects or any objects that have a round or semi-round surface, particularly on a tympanostomy tube for use in a myringotomy procedure.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The surgical grasping instruments with U-shaped jaws is a forceps-like instrument having jaws that are U-shaped. The U-shaped jaws have a substantially semi-circular configuration so that objects having a round, curved, or oval surface are easily yet definitely grasped and held with greater stability. The instrument will provide greater handling, thereby providing better control during manipulation of surgical objects. In particular, ventilation tubes for ears, stents for vessels, and pins or screws for bone and joint reconstruction are among the myriad of surgical objects capable of being handled and manipulated by the present surgical grasping instrument. Also, the instrument can be applied in holding body tissues grafts that have the same round or semi-round shape.

Figure 1:
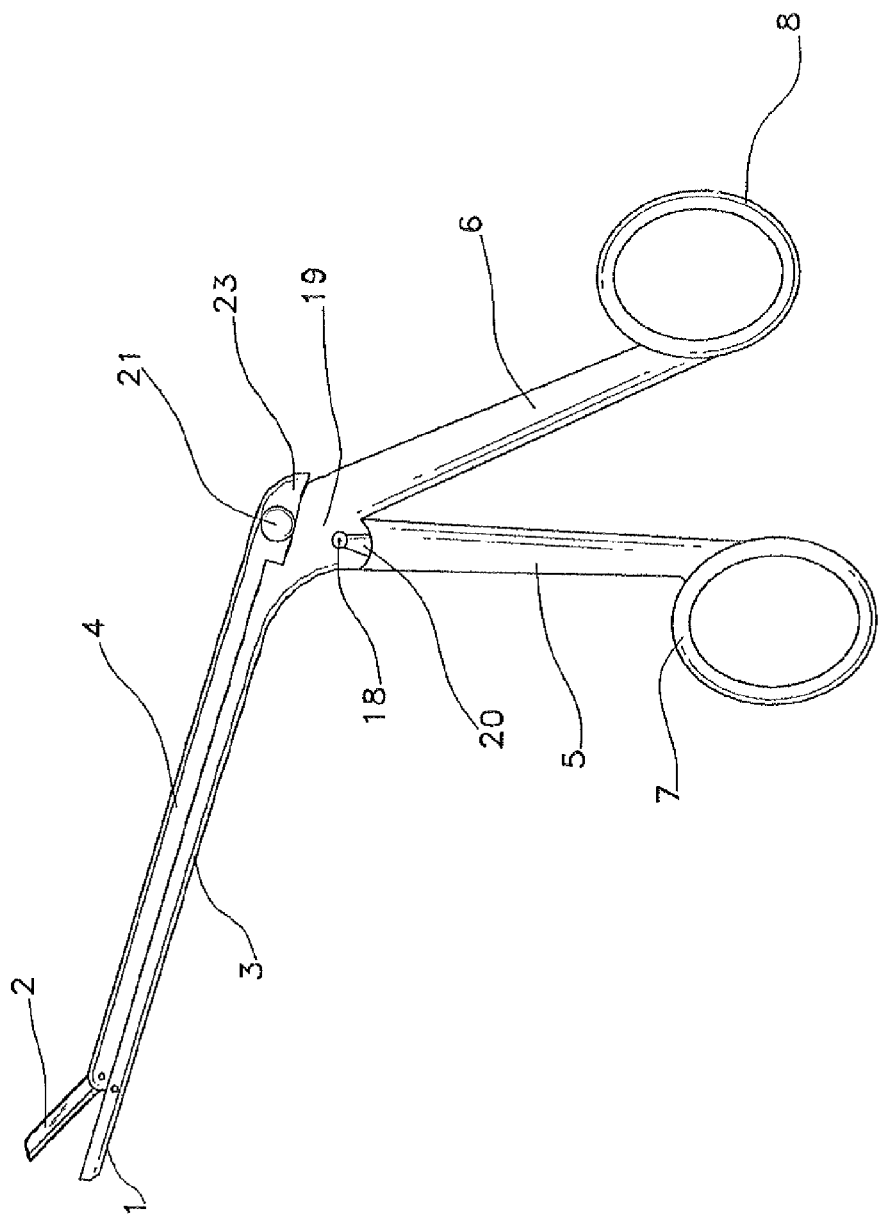
FIG. 1 is a side view of a surgical grasping instrument with U-shaped jaws according to the present invention.
Figure 2:
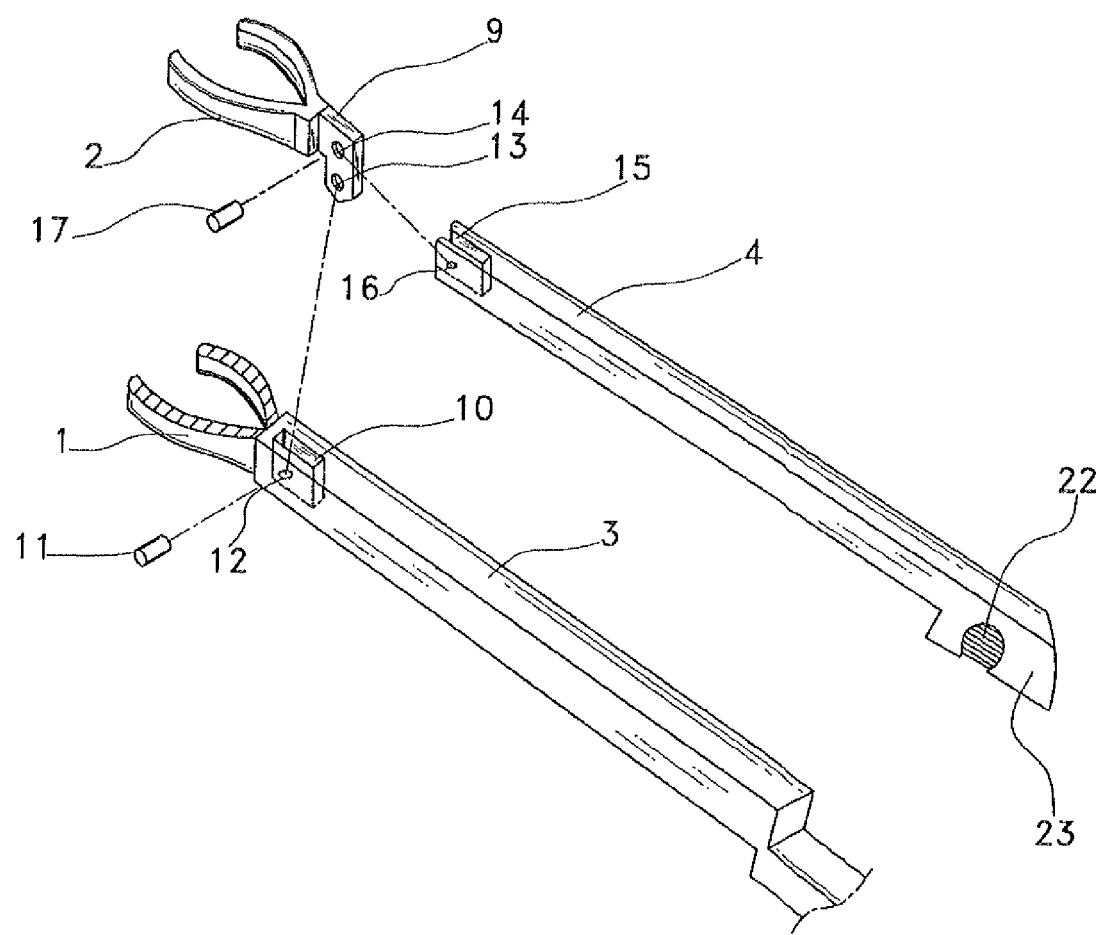
FIG. 2 is a partially exploded perspective view of the anterior ends of the surgical grasping instrument of FIG. 1, showing connection of the jaws to the elongated arms.

As shown in FIGS. 1 and 2, the surgical grasping instrument has a pair of U-shaped jaws 1 and 2, elongated arms 3 and 4, and handles 5 and 6 terminating at one end in finger loop members 7 and 8, by which the surgeon may operate the instrument similar to a scissors by placing a finger and a thumb in the finger loops 7 and 8. The U-shaped jaws 1, 2 are disposed at the ends of the elongated arms 3, 4, and are moveable relative to each other. The arms 3, 4 may extend from the handles 5, 6 at an oblique angle, as shown in the drawings.

FIG. 2 is a partial perspective view of the anterior ends of the instrument of FIG. 1, showing the details both jaws 1 and 2 and how they are mounted at the anterior ends of the elongated arms 3 and 4. The lower jaw 1 is rigidly connected to the anterior end of lower arm 3. The upper jaw 2 is pivotally mounted to the anterior ends of both the lower arm 3 and the upper arm 4. Both grasping surfaces of the jaws 1, 2 are U shaped or double head, and in opposed and identical mirror image to each other. A downwardly extending flange 9 is integral with the posterior end of the upper jaw 2. A vertical slot 10 is defined at the anterior end of the lower arm 3. The flange 9 slidably engages the slot 10. A pair of aligned holes 12 are defined in the anterior end of the lower arm and define a passage extending transversely through the slot 10. A first pivot pin 11 is inserted through the aligned holes 12 and the lower hole 13 defined in the flange 9 so that the upper jaw 2 may pivot on the pin 11, the slot 10 permitting the flange 9 to rotate forward and rearward. Thus, the upper jaw 2 is mounted for pivotal movement toward and away the lower jaw 1.

An upper hole 14 is defined in the upper portion of the flange 9. The upper end of flange 9 is slidably disposed in a vertical slot 15 defined in the anterior end of the upper arm 4. Aligned holes 16 are defined in the anterior end of the upper arm 4 and define a passage extending transversely through the slot 15 in the upper arm. A second pivot pin 17 is inserted through the holes 16 in the upper arm and the upper hole 14 of the flange 9 to provide a pivotal connection between the upper arm 4 and the upper jaw 2. Thus, as the upper arm 4 is slidably moved forward or backward, the second pivot pin 17 constrains the upper jaw 2 to move with it, the first pivot pin 11 providing an anchor pivot constraining the upper jaw 2 to pivot around the first pin 11, the slots 10 and 15 permitting the flange 9 to rock or rotate forward and rearward.

Figure 3:
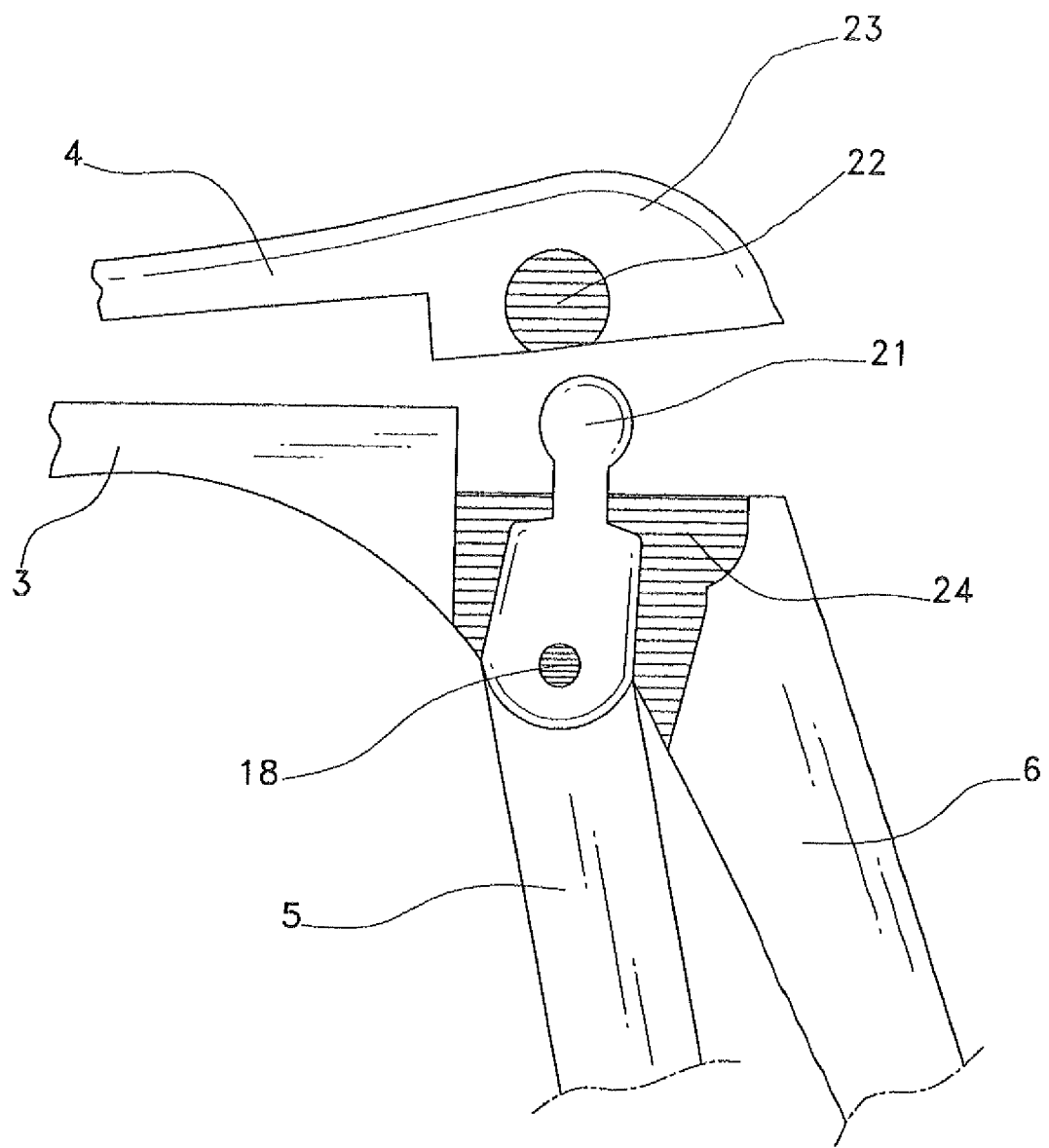
FIG. 3 is a partially exploded diagrammatic side view of the joint between the handles and the elongated arms of the surgical grasping instrument of FIG. 1.

As shown in FIGS. 1 and 3, the forward or anterior handle 5 is pivotally attached to a bridge portion 19 of the rearward or posterior handle 6 by a pivot pin 18. This permits the anterior handle 5 to be moved about the pivot pin 18 reciprocally toward and away from the posterior handle 6 in a plane passing through both of the handles 5,6. Integrally secured to the upper end of anterior handle 5 is round projection or ball 21, which moves back and forth in the same plane as the anterior handle 5 when the handle 5 is moved along at its hinge or pivot point about pin 18. The upper arm 4 has an upper recess or socket 22 along one side of the rear shoulder portion 23 for receiving the ball 21. The ball 21 extends upward and is integral with the anterior handle 5. Thus, as the anterior handle 5 is pivoted, the ball 21 will rotate in the socket 24, the ball and socket joint securing the posterior end of the upper arm 4 to the anterior handle 5 and constraining the upper arm 4 to slide forward and backward in conformity to pivotal movement of the anterior handle 5. During pivoting, the pivot pin 18 moves in a notch 20 cut into the bridge portion 19 of the stationary posterior handle 6. The posterior handle 6 is rigidly connected with the lower arm 3. When the handles 5,6 are squeezed together or moved apart, the jaw operating assembly functions to selectively open and close the jaws 1, 2.

Figure 4:
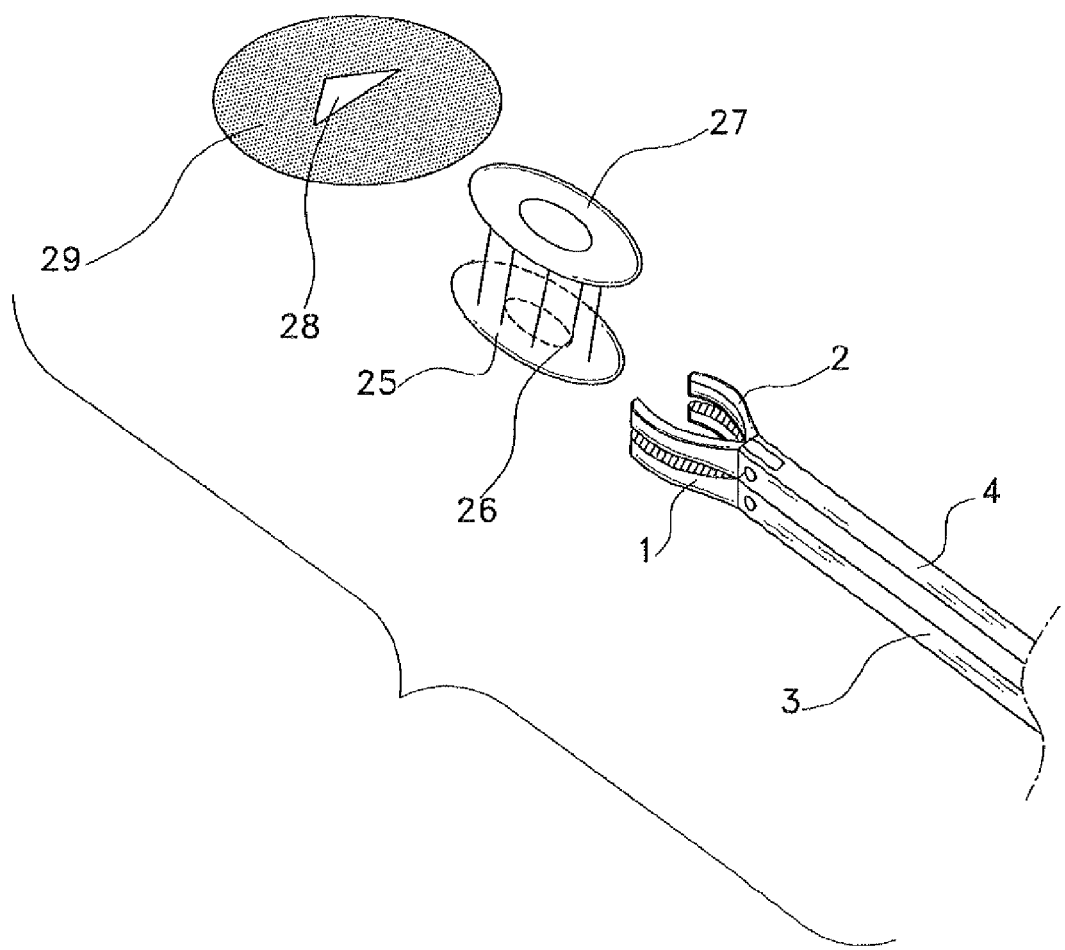
FIG. 4 is an environmental, partial, diagrammatic, exploded perspective view of the surgical grasping instrument of FIG. 1, showing the jaws about to grasp a tympanostomy tube for insertion through a slit in the tympanic membrane.
Figure 5:
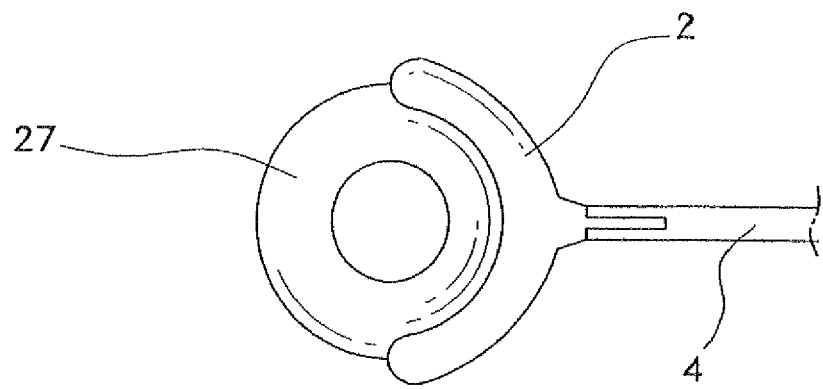
FIG. 5 is an environmental, partial, diagrammatic top view of the surgical grasping instrument of FIG. 1, illustrating the instrument grasping a tympanostomy tube.
Figure 6:
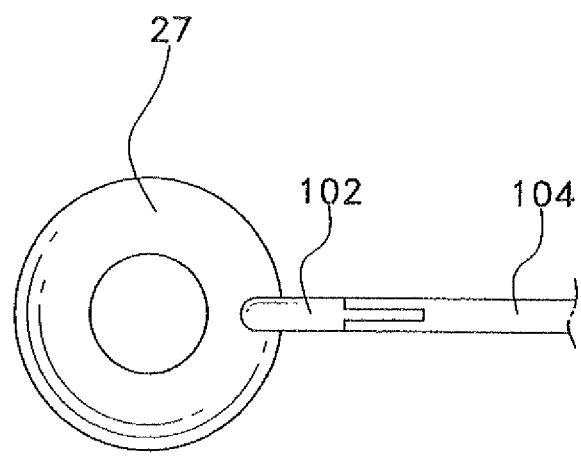
FIG. 6 is an environmental top view of a conventional forceps of the prior art shown grasping a flange of a tympanostomy tube.

As shown in FIGS. 4-6, the U-shaped jaws 1, 2 of the surgical grasping instrument are dimensioned and configured to hold a substantially round or semi-round surface of an object, such as a ventilation ear tube, which consists of a first interior round flange 25 connected to one end of the tubular member 26, and a second round exterior flange 27 connected to the opposite end of the tubular member 26. The U-shaped jaws 1, 2 are designed to fit and grasp the round surface as in FIG. 5, with one jaw 2 shown above the exterior flange 27 and the other jaw 1 (not visible in FIG. 5) below the same flange 27, the jaws 1, 2 being pivoted to clamp the exterior flange 27 therebetween. This is different from the straight or linear jaws 102 extending from the arms 104 of the conventional forceps of the prior art, as the U-shaped jaws 1, 2 provide 180° of support, instead of grasping from a single point on one side of the flange 27, as shown in FIG. 6. Also, as shown in FIG. 4, after inserting one side of the first flange 25 of the ventilation tube in the slit 28 in the tympanic membrane 29, the jaws 1, 2 of the present surgical grasping instrument act as claws that provide a fine-controlled, guided mobility to push the body of ventilation tube in the tympanic membrane slit 28 easily. The faces of the jaws 1, 2 that come into contact with the object being grasped may be smooth, or may be knurled to provide greater frictional contact.

It is to be understood that the present invention is not limited to the embodiments described above, but encompasses any and all embodiments within the scope of the following claims.

I claim:

1. A surgical grasping instrument, comprising:
   upper and lower elongated arms, each &the arms having an anterior end and a posterior end, the arms being maintained in sliding contact;
   upper and lower U-shaped jaws, the lower jaw rigidly extending from the anterior end of the lower arm, the upper jaw being pivotally attached to both the anterior end of the upper arm and the anterior end of the lower arm, the upper jaw pivoting away from the lower jaw when the upper arm slides rearward relative to the lower arm, the upper jaw pivoting towards the lower jaw to grasp an object between the jaws when the upper arm slides forward relative to the lower arm, and
   a forward handle and a rearward handle, each of the handles having a finger loop, the rearward handle being rigidly attached to the posterior end of the lower arm, the forward handle being pivotally attached to the rearward handle and pivotally attached to the upper arm so that pivoting the forward handle relative to the rearward handle slides the upper arm relative to the lower arm, thereby pivoting the upper jaw towards or away from the tower jaw to grasp or release the object;
   wherein said upper and lower jaws are dimensioned and configured to grasp a circular flange of a tympanostomy tube therebetween and position the tympanostomy tube in a slit within a tympanic membrane.

2. The surgical grasping instrument according to claim 1, wherein:
   the lower arm has a first slot defined therein at the anterior end of the lower arm;
   the upper arm has a second slot defined therein extending into the anterior end of the upper arm;
   said upper jaw has a flat flange extending rearward therefrom, the flange having upper and lower holes defined therein, the flange being disposed in the first and second slots;
   the lower arm has a first pivot pin extending transversely through the first slot and the lower hole in the flange, the first pivot pin defining an anchor pivot for said upper jaw; and
   the upper arm has a second pivot pin extending transversely though the second slot and the upper hole in the flange, whereby the second pivot pin constrains said upper jaw to pivot around the anchor pivot when said upper arm slides relative to said lower arm.

3. The surgical grasping instrument according to claim 2, wherein:
   said forward handle has a ball extending therefrom; and
   the posterior end of said upper arm has a socket defined therein, the ball being pivotally mounted in the socket to form a ball and socket joint, whereby pivotal movement of the forward handle results in sliding movement of said upper arm.

4. The surgical grasping instrument according to claim 3, wherein said rearward handle has a bridge portion having a notch defined therein, a portion of said forward handle pivoting in the notch.

5. The surgical grasping instrument according to claim 1, wherein each of said jaws has a smooth grasping face.

6. The surgical grasping instrument according to claim 1, wherein each of said jaws has a knurled grasping face.

7. The surgical grasping instrument according to claim 1, wherein said arms extend from said handles at an oblique angle.

8. The surgical grasping instrument according to claim 1, wherein each of said jaws has a double head.

9. A surgical grasping instrument, comprising:
   upper and lower elongated arms, each of the arms having an anterior end and a posterior end, the arms being maintained in sliding contact;

a forward handle and a rearward handle, each of the handles having a finger loop, the rearward handle being rigidly attached to the posterior end of the lower arm; and upper and lower jaws, the lower jaw rigidly extending from the anterior end of the lower arm, the upper jaw being pivotally attached to both the anterior end of the upper arm and the anterior end of the lower arm, the upper jaw pivoting away from the lower jaw when the upper arm slides rearward relative to the lower arm, the upper jaw pivoting towards the lower jaw to grasp a substantially elliptical object between the jaws when the upper arm slides forward relative to the lower arm;

the upper and lower jaws each extending symmetrically and transversely from the attachment having a U-shaped form; the upper and lower jaws being aligned along the U-shaped form, the U-shaped form spanning an arc of 180°;

wherein the forward handle being pivotally attached to the rearward handle and pivotally attached to the upper arm so that pivoting the forward handle relative to the rearward handle slides the upper arm relative to the lower arm, thereby pivoting the upper jaw towards or away from the lower jaw to grasp or release the object;

wherein the object is a tympanostomy tube, and the upper and lower jaws are dimensioned and configured to grasp a flange end of the tympanostomy tube therebetween and position the tympanostomy tube in a slit within a tympanic membrane.

10. The surgical grasping instrument according to claim 9, wherein each of said jaws has a smooth grasping face.

11. The surgical grasping instrument according to claim 9, wherein each of said jaws has a knurled grasping face.

12. A surgical instrument in combination with a tympanostomy tube, comprising:

a tympanostomy tube having an elliptical flange at each end thereof;

a pair of handles each having a finger loop;

a pair of elongated arms, arranged and configured to be maintained in sliding contact, each of the elongated arms having an anterior end and a posterior end, the arms being respectively and operatively coupled to the pair of handles at the posterior end thereof;

an upper jaw and a lower jaw, the upper and lower jaws being respectively and operatively coupled to the pair of anterior ends of the elongated arms;

the upper and lower jaws each extending symmetrically and transversely from the elongated arms having a U-shaped form, the upper and lower jaws being aligned along the U-shaped form, the U-shaped form spanning an arc of 180°;

wherein the substantially elliptical flange of the tympanostomy tube being grasped, manipulated, and released by the upper and lower jaws along an arcuate edge of the flange.

* * * * *